US006885003B1

(12) United States Patent
Dubernet

(10) Patent No.: US 6,885,003 B1
(45) Date of Patent: Apr. 26, 2005

(54) METHOD AND DEVICE FOR OBJECTIVE QUALITATIVE ANALYSIS OF GRAPE MUST AND/OR WINES USING WIDEBAND INFRARED SPECTROMETRY

(75) Inventor: Marc Dubernet, Narbonne (FR)

(73) Assignee: Foss Electric A/S, Hillerod (DK)

( * ) Notice: Subject to any disclaimer, the term of this patent is extended or adjusted under 35 U.S.C. 154(b) by 312 days.

(21) Appl. No.: 10/049,819

(22) PCT Filed: Aug. 17, 2000

(86) PCT No.: PCT/DK00/00455
§ 371 (c)(1),
(2), (4) Date: Jun. 24, 2002

(87) PCT Pub. No.: WO01/14857
PCT Pub. Date: Mar. 1, 2001

(30) Foreign Application Priority Data

Aug. 19, 1999 (FR) .......................................... 99 10627

(51) Int. Cl.[7] ........................ G01N 21/35; G01N 33/14
(52) U.S. Cl. ............................ 250/339.09; 250/339.08
(58) Field of Search ..................... 250/339.09, 339.07, 250/339.08, 339.1, 339.12, 341.5, 343, 338.5, 252.1

(56) References Cited

U.S. PATENT DOCUMENTS

| | | | | |
|---|---|---|---|---|
| 4,228,192 A | | 10/1980 | Sanden | |
| 5,187,368 A | * | 2/1993 | Galante et al. .......... | 250/341.5 |
| 5,679,955 A | * | 10/1997 | Schmidt et al. ............. | 250/343 |
| 6,070,128 A | * | 5/2000 | Descales et al. .............. | 702/30 |
| 6,690,015 B1 | * | 2/2004 | Benes et al. ........... | 250/339.12 |
| 2001/0050339 A1 | * | 12/2001 | Panigrahi et al. ...... | 250/339.07 |

FOREIGN PATENT DOCUMENTS

| | | |
|---|---|---|
| EP | 0 543 722 A1 | 11/1992 |
| EP | 0 706 040 A1 | 4/1996 |
| EP | 0 760 479 A2 | 3/1997 |
| WO | WO 96 11399 A | 4/1996 |

OTHER PUBLICATIONS

Cabanis et al., "L'Infraalyzer 400: Une Determination Automatique Du Titre Alcoometrique Des Vins", Compagnie Technicon, 95330 Domont, pp 75–79.
International Search Report.
Gishen et al., "Some preliminary trails in the applications of scanning near infrared spectroscopy (NIRS) for determining the compositional quality of grape, wine and spirits", The Australian Grapegrower & Winemaker 414(A) 43 (1998).
The Australian Wine Research Institute Annual Report 1999, p. 7, paragraph 8.
Lendl et al, "A rapid automated method for wine analysis based upon FT–IR spectroscopy" Institute of Analytical Chemistry, Vienna University of Technology, Getreidemarld 9/151, A–1060 Vienna, Austria pp 59–68.
Australian Office Action.

* cited by examiner

*Primary Examiner*—David Porta
*Assistant Examiner*—Faye S. Polyzos
(74) *Attorney, Agent, or Firm*—Harness, Dickey & Pierce, P.L.C.

(57) ABSTRACT

The invention concerns a method and a device for the objective qualitative analysis of liquid vinification compositions, comprising memory means (8) in which are recorded calibrating values of spectroscopic criteria for a group of characteristic parameters comprising the concentration levels of at least a compound produced by *Botrytis cinerea*, at least a compound produced by yeasts, at least a compound produced by the acetic bacteria, and at least a compound produced by lactic acid bacteria, means (1, 2, 3, 4, 6) for producing a continuous infrared spectrum, and means (7) for calculating the value ($V_P$) of each characteristic parameter in the composition from the spectrum.

23 Claims, 2 Drawing Sheets

METHOD AND DEVICE FOR OBJECTIVE QUALITATIVE ANALYSIS OF GRAPE MUST AND/OR WINES USING WIDEBAND INFRARED SPECTROMETRY

BACKGROUND OF THE INVENTION

1. Field of the Invention

The invention relates to a method and a device for objective qualitative analysis by broadband infrared spectrometry of grape musts intended for vinification and/or wines, collectively referred to in this text as "vinification compositions".

2. Description of the Related Art

For a long time a solution has been sought that would permit an objective and rapid qualitative evaluation of grape musts intended for vinification. Such an evaluation would make it possible to determine objectively the price of a grape harvest according to its quality. Furthermore, it would be possible to better select the musts according to the qualities of the desired wines, and ultimately to employ vinification technologies that are better adapted to the quality of the grape musts. To be effective this objective analysis must be able to be carried out very quickly (within no more than about 1 to 2 minutes) on the raw musts at the vinification sites (and not only in a laboratory).

Until now the musts have been evaluated in a coarse manner, essentially by measuring the content of sugar by refractometry or densitometry. In rare cases this measurement has been supplemented by measuring the total acidity and the pH by traditional chemical titration methods. Sometimes a subjective semi-quantitative evaluation of the presence of laccase, (an enzyme secreted by *Botrytis cinerea*, a grape parasite) is carried out. Nevertheless, as this enzyme itself is destroyed by the products of the reactions that it catalyses, its measurement is not useful.

The same problem arises for the objective qualitative analysis of wines that would permit an objective determination of their value and the qualities.

It has been proposed to determine the alcoholic strength of wines by using a spectrophotometer in the near infrared range for 19 distinct wavelengths ("l'infraalyzer 400: une determination automatique du titre alcoometrique des vins" CABANIS et al, Fran . . . Oenol 89, 75–79.1983).

Nevertheless, the use of such an apparatus is long and complex, only provides results for the measurement of ethanol and sugar reducing agents, and does not permit a complete objective analysis of the quality of the musts and/or the wines.

For more than 20 years, various other theoretical methods of analysis of grape musts and/or wines have been described, but none of them has become the object of practical exploitation. They are much too complex to put into practice and/or do not provide complete and reproducible objective results.

SUMMARY OF THE INVENTION

The invention aims to remedy these drawbacks by proposing a method and a device permitting the provision of an objective qualitative analysis of grape musts and/or wines and capable of being put into practice outside a laboratory-particularly at a vinification site.

The invention aims then to permit this analysis to be obtained in a rapid manner, particularly within a maximum duration of 1 to 2 minutes.

The invention also permits this analysis to be obtained in a simple automatic manner, in a single analysis step performed automatically, without it being necessary to carry out chemical preparations, manipulations or adjustments.

The invention also aims to permit reliable and complete analyses to be obtained permitting an objective appreciation of the quality of a wine and/or must and/or the harvest from which a must originates, in a manner particularly enabling an objective determination of its price and facilitating the defining of the subsequent measures to be taken for the vinification and/or the conservation and/or the commercialisation.

To achieve this, the invention concerns a method for the objective qualitative analysis of liquid vinification compositions, characterised in that an initial configuration and calibration step (13) is carried out during which:
a group of characteristic parameters are selected that are capable of characterising the quality of a vinification composition to be analysed, and comprising the concentration levels in the vinification composition of characteristic compounds chosen among at least a compound produced by *Botrytis cinerea*, at least a compound produced by yeasts, at least a compound produced by acetic bacteria, and at least a compound produced by lactic acid bacteria,
calibration values of spectroscopic criteria are determined and recorded for each characteristic parameter, the spectroscopic criteria being chosen to enable evaluation of the characteristic parameter in a vinification composition from an infrared absorption spectrum, which can be generated on a sample of this vinification composition,
for each vinification composition to be analysed:
a spectroscopic analysis is carried out during which a continuous Infrared absorption spectrum of a sample of this vinification composition is generated.
the spectroscopic criteria of each characteristic parameter are applied to the said continuous spectrum in such a way that the value of this characteristic parameter in the vinification composition is evaluated by automatic calculation.

Advantageously and according to the invention, the group of characteristic parameters comprises the concentration of each of the characteristic compounds belonging to the group consisting of gluconic acid, ethanal, ethyl acetate, arabitol, mannitol, sorbitol, 2,3-butanediol, methyl-3 butanol-1, glycerol, mesoinositol and isoamyl acetate. Thus calibration values are determined and recorded for these characteristic parameters, which are evaluated by calculation for each vinification composition to be analysed.

Advantageously and according to the invention, the spectroscopic criteria are chosen to enable evaluation of each characteristic parameter in a vinification composition from a near and mid infrared absorption spectrum, and the near and mid infrared continuous spectrum of each vinification composition to be analysed is generated.

Advantageously and according to the invention, the continuous spectrum is generated by Fourier transform interferometric spectroscopy.

Advantageously and according to the invention, at least an objective quality index of the vinification composition is calculated automatically as a function of the said value evaluated from at least a characteristic parameter for the vinification composition to be analysed. Advantageously and according to the invention the function is a polynomial function.

Advantageously and according to the invention the following are calculated:
- a first quality index, representing the attack on the harvest by *Botrytis cinerea*, at least as a function of the value of concentration levels of gluconic acid, mannitol and sorbitol evaluated from the continuous spectrum by application of spectroscopic criteria,
- a second quality index, representing the attack by yeasts, at least as a function of the value of the concentration levels of ethanal, ethyl acetate, arabitol, 2,3-butanediol, methyl-3 butanol-1, glycerol, and isoamyl acetate, evaluated from the continuous spectrum by application of spectroscopic criteria,
- a third quality index representing the attack by acetic bacteria, at least as a function of values of the concentration levels of acetic acid, ethyl acetate and of 2,3-butanediol evaluated from the continuous spectrum obtained by application of spectroscopic criteria,
- a fourth quality index representing the attack by lactic acid bacteria, at least as function of the value of concentration levels of lactic acid, mannitol and of 2,3-butanediol, evaluated from the continuous spectrum by application of spectroscopic criteria,
- and a fifth quality index representing the fermentation ability, at least as a function of the value of the concentration level of mesoinositol.

Advantageously and according to the invention each characteristic parameter is evaluated and each quality index is calculated by data processing immediately after the spectroscopic analysis step has been carried out.

Advantageously and according to the invention, the spectroscopic criteria comprise for each characteristic parameter, for a selection of an integral number N of spectral bands σi of predetermined wavelengths, the value of the luminescence spectral density Li of the said continuous spectrum, and a value VP of the characteristic parameter is calculated according to the formula:

$$V_p = Bo + \sum_{i=1}^{N} Ki \; Li$$

where Bo and Ki are predetermined coefficients. Advantageously and according to the invention, N is included in the group from 5 to 30—particularly in the order 15–.

Advantageously and according to the invention the group of characteristic parameters further comprises the alcoholic volumetric strength; total sugar content; total acidity; pH; concentration of acetic acid; concentration of malic acid; concentration of tartaric acid; concentration of lactic acid, and content of phenolic compounds. In this way the calibration values are determined and recorded for the characteristic parameters which are evaluated by calculation for each vinification composition to be analysed. These characteristic parameters may then also be used and evaluated to determine one or more quality indices.

The invention also extends to a device for carrying out a method according to the invention.

Accordingly, the invention also concerns a device for objective qualitative analysis of liquid vinification compositions, characterised in that it comprises:
- memory means wherein calibration values of spectroscopic criteria are recorded for a group of characteristic parameters capable of characterising the quality of a vinification composition to be analysed, the group comprising the concentration levels in the vinification composition of characteristic compounds selected among at least a compound produced by *Botrytis cinerea*, at least a compound produced by yeasts, at least a compound produced by acetic bacteria, and at least a compound produced by lactic acid bacteria, the said spectroscopic criteria being selected for each characteristic parameter to enable evaluation of the characteristic parameter in a vinification composition from an infrared absorption spectrum that can be generated on a sample of this vinification composition,
- spectroscopic analysis means for collecting a vinification composition sample and generating an infrared continuous spectrum of this sample,
- calculation means arranged to apply the spectroscopic criteria of each characteristic parameter to the said continuous spectrum and to evaluate by automatic calculation the value of this characteristic parameter in the vinification composition.

Advantageously and according to the invention, the group of characteristic parameters comprises the concentration of each of the characteristic compounds belonging to the group consisting of gluconic acid, ethanal, ethyl acetate, arabitol, mannitol, sorbitol, 2,3-butanediol, methyl-3butanol-1, glycerol, mesoinositol and isoamyl acetate. Then calibration values of these concentration levels are recorded in the memory means and the calculation means are arranged to evaluate the value of these characteristic parameters.

Advantageously and according to the invention, the selection criteria are chosen for each characteristic parameter to enable evaluation of the characteristic parameter in a vinification composition from a near and mid infrared spectrum, and the means for spectroscopic analysis are arranged to generate the near and mid infrared continuous absorption spectrum. Advantageously and according to the invention, the means for spectroscopic analysis comprise a Fourier transform interferometric spectrometer.

Advantageously and according to the invention, the calculation means are arranged to calculate automatically at least an objective quality index of the vinification composition as a function of said value evaluated from at least a characteristic parameter for the vinification composition to be analysed. Advantageously and according to the invention, the function is a polynomial function.

Advantageously and according to the invention the calculation means are arranged to calculate:
- a first quality index, representing the attack on the harvest by *Botrytis cinerea*, at least as a function of the value of concentration levels of gluconic acid, mannitol and sorbitol evaluated from the continuous spectrum by application of spectroscopic criteria,
- a second quality index, representing the attack by yeasts, at least as a function of the value of the concentration levels of ethanal, ethyl acetate, arabitol, of 2,3- butanediol, of methyl-3 butanol-1, of glycerol, and of isoamyl acetate evaluated from the continuous spectrum by application of spectroscopic criteria, a third quality index representing the attack by acetic bacteria, at least as a function of values of the concentration levels of acetic acid, ethyl acetate and of 2,3-butanediol evaluated from the continuous spectrum obtained by application of spectroscopic criteria, a fourth quality index representing the attack by lactic acid bacteria, at least as function of the value of concentration levels of lactic acid, mannitol and of 2,3-butanediol, evaluated from the continuous spectrum by application of spectroscopic criteria, and a fifth quality index representing the fermentation ability, at least as a function of the value of the concentration level of mesoinositol.

Advantageously and according to the invention, the calculation means are arranged to evaluate each characteristic parameter and to calculate each quality index by data processing immediately after the generation of the continuous spectrum by the spectroscopic analysis means, and to provide the results of these calculations to means that are read by a user. Advantageously and according to the invention, the means that are read comprise means for printing a report of results.

Advantageously a device according to the invention, is characterised in that for each characteristic parameter, the calibration values comprise an integral number N of spectral bands σi of predetermined wavelengths, and coefficients Ki and Bo, and in that calculation means are arranged to calculate a value $V_p$ of the characteristic parameter from the values of the luminescence spectral density Li of the said continuous spectrum obtained for the N spectral bands ai according to the formula, $$V_p = Bo + \sum_{i=1}^{N} Ki \; Li$$

Advantageously and according to the invention N lies between 5 and 30, particularly in the order of 15.

Advantageously and according to the invention, the group of characteristic parameters further comprises the volumetric alcoholic strength; total sugar content; total acidity, pH; concentration of acetic acid; concentration of malic acid; concentration of tartaric acid; concentration of lactic acid, and content of phenolic compounds. Calibration values of these concentration levels are then recorded in the memory means and the calculation means are arranged to evaluate the value of the characteristic parameters.

The invention also concerns a method and a device in combination with all or with part of the above or below mentioned characteristics.

In a method according to the invention, the initial configuration and calibration step is carded out once and for all, e.g. in the factory when manufacturing the device according to the invention. Afterwards, the analysis of each vinification composition is obtained in a single automatic, simple and rapid step.

Accordingly, the invention permits one to obtain an analysis of a vinificabion composition in a simple, rapid, reliable objective and automatic manner. In particular, it should be noted that the inventors have found that among the multitude of different compounds figuring in the composition of the vinification compositions, the characteristic parameters chosen in a method according to the invention are specific to a quality index, and can be measured in practice by infrared spectroscopy from a continuous spectrum in a meaningful and useful manner, particularly by Fourier transform Interferometric spectrometry.

The inventor has also found that this technology, even though on the face of it, it is considered one of the most complex within the area of spectrometry, particularly as it normally requires the carrying out of calibrations, Adjustments, and heavy and complex calculations, can in fact provide rapid and precise results when it is applied to a vinification composition. Particularly, even though, on the face of it, it appears much more burdensome and complex than the use of the previously proposed spectrometer with 19 distinct wavelengths, on the contrary, the invention has proved able to permit, after configuration and calibration, a complete objective reliable and rapid analysis to be obtained. Further, the inventor has found that it is possible to provide the results directly in synthesised and simplified form in a few indices of quality that easily can be interpreted by vinification professionals.

BRIEF DESCRIPTION OF THE DRAWINGS

Other objects advantages and characteristics of the invention will appear from the reading of the examples in the following description with reference to the drawings in which.

DETAILED DESCRIPTION

Figure 1:
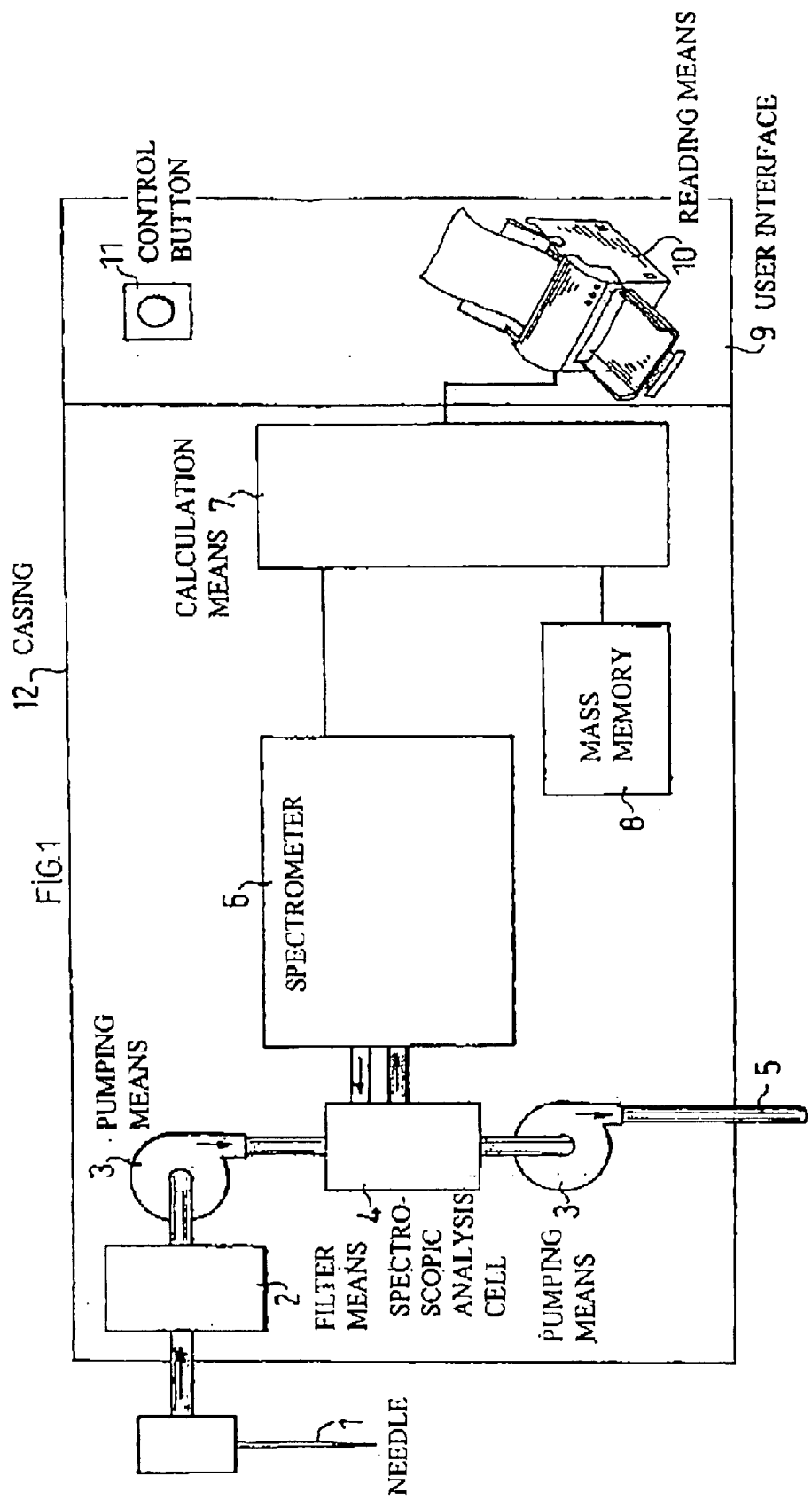
FIG. 1 is a schematic diagram of a device according to the invention.

FIG. 1 illustrates a device according to the invention comprising a needle 1 for extraction of a liquid vinification composition sample for which an objective qualitative analysis is desired. This extraction needle 1 is connected to filter means 2 and to means 3 for pumping a predetermined quantity of vinification composition forming the sample to be analysed, permitting the introduction of this sample into a spectroscopic analysis cell 4. The pumping means 3 are motorised and automatically controlled to extract the predetermined quantity of liquid vinification composition and maintain it in the cell 4 for a period of time to permit the generation of a continuous infrared absorption spectrum of the sample in the cell 4. These pumping means 3 can be formed in any known manner from an automatic control device, one or more electric motors and pumps, particularly peristaltic pumps. A pump can be provided upstream of the cell 4 to introduce the sample into this cell 4, and another pump can be provided downstream from the cell 4 to remove the sample from the cell 4 after analysis and move it towards a discharge outlet 5 as shown in FIG. 1.

Also the device according to the invention comprises a Fourier transform interferometric spectrometer 6 arranged to generate a continuous infrared absorption spectrum —particularly in the near or mid infrared range, i.e. for wavelengths comprising 800 nm and 15000 nm—of the sample in the cell 4. Such a Fourier transform interferometric spectrometer providing a continuous near or mid infrared absorption spectrum is known as such. In particular, the spectrometer FT 120 sold by FOSS FRANCE SA (Nanterre, France) can be cited. Such an interferometer is fully automatic and incorporates means for calculating the continuous spectrum by Fourier transformation from the generated interferogram, and software for using the data. Furthermore, these calculation means are arranged to provide the results of the continuous spectrum in the form of numerical data, which can be input directly into the microprocessor data processing means 7 of the device according to the invention.

The data processing means 7 are arranged and programmed to carry out the different calculations of a method according to the invention. A mass memory 8, such as a hard disk and/or a disk or diskette reader is associated with the data calculation means 7, which also comprises the assembly of electronic components and the various customary peripherals which are necessary for their operation and which are not shown in FIG. 1.

In the mass memory 8 are recorded the calibration values of spectroscopic criteria for a group of characteristic parameters characterising the quality of a vinification composition to be analysed, this group comprising the concentration in the vinification composition of characteristic compounds chosen among at least a compound produced by *Botrytis cinerea*, at least a compound produced by yeasts, and at least a compound produced by acetic bacteria, at least a compound produced by lactic acid bacteria, the said spectroscopic criteria being selected for each characteristic parameter to permit evaluation of the characteristic parameter in a vinification composition from an infrared absorption spectrum which can be generated on a sample of the vinification composition.

Furthermore. The data processing means 7 are arranged to apply each spectroscopic criterion of each characteristic parameter to the continuous spectrum produced by the interferometer spectrometer 6 and to evaluate by automatic calculation the value of the characteristic parameter in the vinification composition located in the cell 4.

In particular for each characteristic parameter the calibration values stored in the mass memory 8 comprise coefficients $K_i$ to be applied to the luminescence spectral density values $L_i$ of the continuous spectrum obtained for different spectral bands $\sigma_i$ of predetermined wavelengths. And the data processing means 7 calculate the value $V_P$ of the characteristic parameter according to the formula:

$$V_p = Bo + \sum_{i=1}^{N} Ki \ Li$$

where N is the integral number of retained spectral bands, which preferably lies between 5 and 30, in particular in the order of 15.

The various calibration values are established for each characteristic parameter from a statistic analysis of a large number of known reference samples from vinification compositions in which the real value of the characteristic parameter is known, e.g. predetermined by measured amounts added or physical-chemical measurement in a laboratory.

The statistical correlation between the continuous spectra obtained for the various vinification compositions and the known real values of each characteristic parameter allowing a determination of the various coefficients $K_i$, can be determined from a statistical calculation made by means of a known statistical calculation program, in particular a statistical spectroscopic program such as the one marketed by the company FOSS FRANCE SA (Nanterre, France).

It should be noted that the inventor has determined that from a certain number of vinification composition reference samples originating from principal grape vines (particularly Chardonnet, Cabernet, Sauvignon. Merlot, Carignan, Syrah, . . . ) and having different sanitary and maturity qualities, an almost universal calibration can be obtained enabling evaluation of characteristic parameters for all vinification compositions with a good reliability.

But the choice, the number, and the characteristics (origin, grape vines, vinification methods, . . . ) of the vinification composition reference samples can also be arranged, according to the same characteristics (origin, grape vines, vinification method, . . . ) of the vinification compositions to be analysed for optimising the calibration. For example, it is possible to supplement the initial calibration with reference samples from vinification compositions provided from the same wine-rowing region as the vinification compositions that have to be analysed.

The calculation means 7 are also arranged to calculate automatically at least one objective quality index of the vinification composition as a function of the value of at least one characteristic parameter. More particularly according to the invention, the calculation means 7 are arranged to calculate:

a first quality index $Q_1$, representing the attack of the harvest by *Botrytis cinerea*, at least as a function of the value of concentration levels of gluconic acid, mannitol and sorbitol evaluated from the continuous spectrum by application of spectroscopic criteria, a second quality index $Q_2$, representing the attack by yeasts, at least as a function of the value of the concentration levels of ethanal, ethyl acetate, arabitol, of 2,3-butanediol, of methyl-3 butanol-1, of glycerol, and of isoamyl acetate evaluated from the continuous spectrum by application of spectroscopic criteria, a third quality index $Q_3$ representing the attack by acetic bacteria, at least as a function of values of the concentration levels of acetic acid, ethyl acetate and of 2,3-butanediol evaluated from the continuous spectrum obtained by application of spectroscopic criteria, a fourth quality index $Q_4$ representing the attack by lactic acid bacteria, at least as function of the value of concentration levels of lactic acid, mannitol and of 2,3-butanediol, evaluated from the continuous spectrum obtained by application of spectroscopic criteria, and a fifth quality index $Q_5$ representing the fermentation ability, is calculated at least as a function of the value of the concentration of mesoinositol.

More particularly, each quality index $Q_j$ is calculated as a polynomial function of various characteristic parameters. Furthermore, one or more other general quality indices can be established from the volumetric alcoholic strength, total sugar content, total acid, pH, concentration of malic acid and tartaric acid, and the content of phenolic compounds.

The calculation means 7 are advantageously arranged to evaluate each characteristic parameter and to calculate automatically each quality index $Q_i$ by data processing, and this is done immediately after the generation of the continuous spectrum by the interferometric spectrometer 6.

The choice of the various quality indices $Q_j$ and their calculation formulas from the values of the characteristic parameters can vary to a certain degree according to the nature of the vinification composition (must and/or wine) or according to the characteristics (origin, grape vine, vinification methods . . . ) of the vinification compositions to be analysed.

Nevertheless, the inventors have determined that in practice the pertinent calibration values of the various abovementioned characteristic parameters can be defined by an integral number N of wavelengths lying between 5 and 30, particularly in the order of 15— permitting calculation of the same quality indices $Q_i$ by the same calculation formulas which remain valid for the majority of musts and wines that can be encountered.

In practice, the general character of the calculations depends on the number of vinification composition samples which were used to establish by statistical methods the calibration values, and of the sophistication of the spectroscopic criteria employed, i.e. in particular the number of wavelengths used for each parameter. This number of wavelengths N can vary from one parameter to another, or can, on the contrary—be the same for all the characteristic parameters. The higher it is, the longer are the subsequent data processing calculations to be carried out on the continuous spectrum.

With the actual data means it has been determined that for a number N=15, for the various characteristic parameters mentioned above, it is possible to obtain results of quality indices in less than one minute.

The various calibration values Ki and Bo may be statistically determined either by a multiple linear regression or preferably, by a PLS calculation ("Partial least square"). The calibration values may also comprise corrections of slope and ordinate at the initial origin, i.e. constants α and β to be applied to the above mentioned value $V_P$, according to each characteristic parameter, according to the formula α. $V_P$+β, wherein these constants will vary from one device to another, particularly to compensate for the respective drifts for each interferometric spectrometer 6. The quality indices are thus calculated from the corrected values α. $V_p$+β.

The results of the analysis are communicated by the data processing means 7 to a user interface 9 comprising reading means 10 including means for printing a report with results and/or a display screen. Preferably, the results are communicated in the form of a list of the various calculated quality indices Qj. Preferably, the report also shows the date and/or time of the analysis and identification information for the analysed vinification composition sample. Advantageously, the user interface 9 also comprises a control button 11 permitting initiation of the extraction of a sample through the needle 1, spectroscopic analysis of the sample, and the calculation of the quality indices.

The device according to the invention is particularly compact, simple and reliable to use. Particularly it should be noted that all of the above-mentioned units except the extraction needle 1 and the user interface 9 can be integrated inside a closed casing 12. The user only has to locate the extraction needle 1 in the sample contained in a container, and then operate the control button 11. After a wait of a few seconds, in the order of one to two minutes at the most, he will receive the results from the reading means 10 in the form of a list of quality indices.

Figure 2:
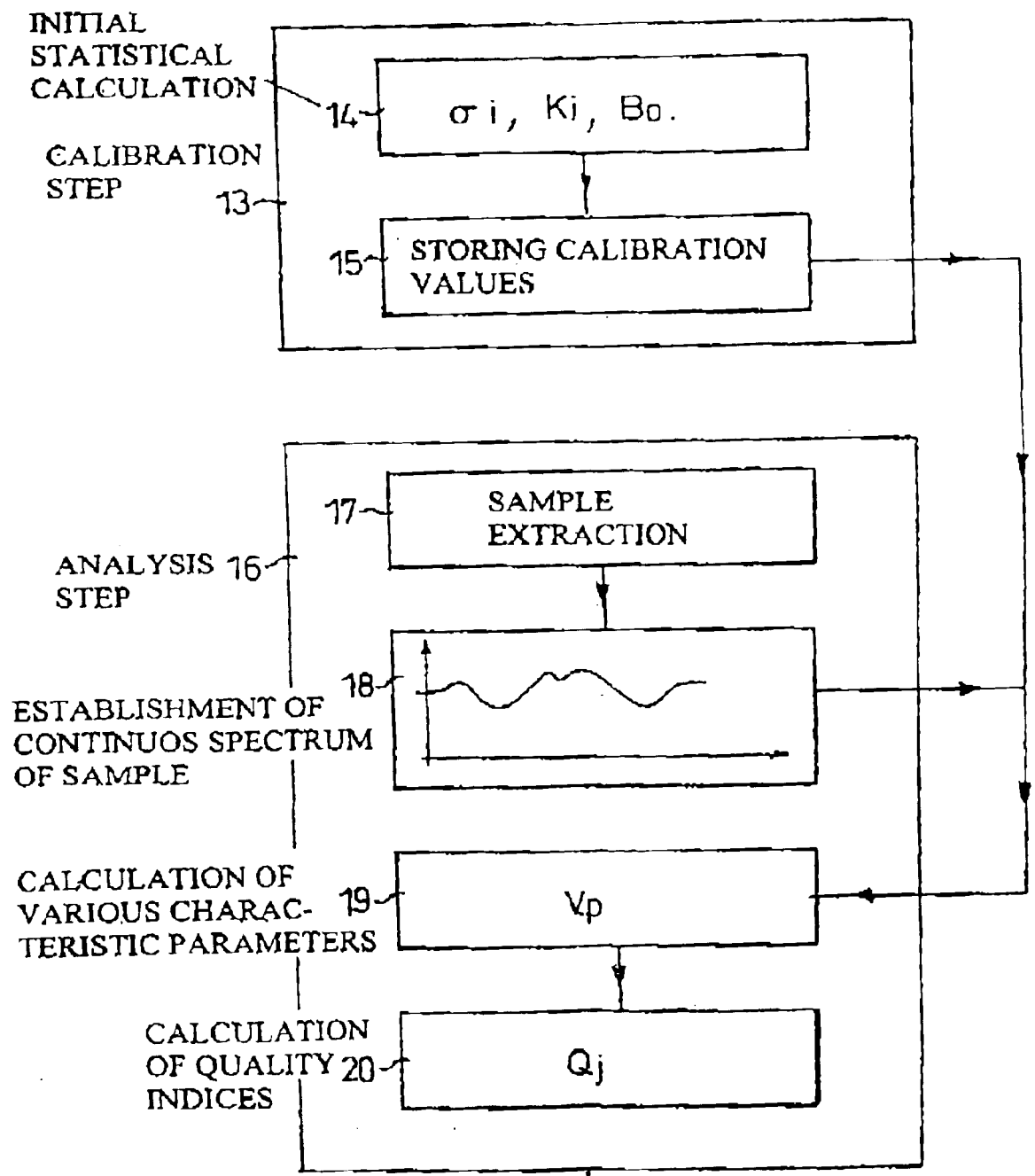
FIG. 2 is a flow diagram of a method according to the invention.

FIG. 2 represents a flow-diagram of an analysis method according to the invention. The method comprises an initial configuration and calibration step 13 during which the device according to the invention is prepared to enable its operation. In this initial step 13, the various characteristic parameters used to characterise the quality of a vinification composition to be analysed later are first chosen. These characteristic parameters are those that were mentioned above. For each characteristic parameter, the N spectral bands σi are chosen, and by statistical calculations the various calibration values Ki, Bo for the various spectral bands ai are determined, and this is done by analysing a multitude of vinification compositions for which the values of the characteristic parameters are known by other means. This initial statistical calculation is carried out during step 14. In the following step 15 the various calibration values i, Ki and Bo are stored in the mass memory 8. Once this initial configuration and calibration step 13 has been performed, the device is ready to function, i.e. it is ready to carry out the analysis of a vinification composition in step 16. In this analysis step 16, at first, a sample extraction 17 is carried out, and then the continuous spectrum of this sample is established 18 with the aid of the Fourier transform interferometer spectrometer 6. From this spectrum and the previously stored calibration values ai, Ki and Bo, the various values $V_P$ of the various characteristic parameters are calculated in step 19 for the various spectral bands ai. Then in step 20 the various quality indices $Q_i$ are calculated from the various values $V_P$ of the characteristic parameters, and these quality indices are delivered to the reading means 10.

EXAMPLE

For each characteristic parameter a series of several samples is generated from musts or wines by adding measured amounts of the compound corresponding to this characteristic parameter. The generated samples then serve to provide the initial configuration and calibration step for a device according to the invention. The various spectroscopic analyses are performed by the interferometer spectrometer FT 120 from the company FOSS FRANCE SA, and the statistical calculations are performed by the spectral statistical analysis programs sold with this device.

The following tables show wavelengths (by pin number) defining the spectral bands i an σ the calibration coefficients Ki and Bo for the spectral bands i—obtained from the samples with measured added amounts for each characteristic parameter. Also the coefficients and of correction corresponding to the apparatus used are given.

The tables also show the discrimination rate of concentration levels obtained with the number of spectral bands σi used.

Furthermore, the same samples are used to re-evaluate according to the invention their respective concentration levels in compounds corresponding to the characteristic parameter. The tests are repeated. The values obtained are compared to values corresponding to the measured added amounts provided in each sample, which are theoretical values. With these values is obtained a calculated standard deviation ETC, and a coefficient of correlation $R^2$ also given in each table.

The same tests are performed in similar manner for ethanal, arabitol, methyl-3 butanol-1, isoamyl acetate, glucerol, 2,3 butanediol, ethyl acetate, mannitol, sorbitol, gluconic acid, and mesonisitol.

The same results can also be obtained with lactic acid, malic acid, tartaric acid, glucose and furctose, total acidity, pH, acetic acid, the total alcoholic content, and the content of phenolic

ETHANAL

| $\sigma i$ | DE | A | Ki | |
|---|---|---|---|---|
| $\sigma$ 1 | 445 | 445 | K 1 | 102675.16746 |
| $\sigma$ 2 | 451 | 451 | K 2 | −123721.54770 |
| $\sigma$ 3 | 375 | 375 | K 3 | −42146.44657 |
| $\sigma$ 4 | 359 | 360 | K 4 | −14287.71152 |
| $\sigma$ 5 | 308 | 309 | K 5 | −28381.96828 |
| $\sigma$ 6 | 294 | 295 | K 6 | 83899.61893 |
| $\sigma$ 7 | 557 | 557 | K 7 | 42104.33149 |
| $\sigma$ 8 | 263 | 272 | K 8 | −16677.82213 |
| $\sigma$ 9 | 400 | 400 | K 9 | 32694.87756 |
| $\sigma$ 10 | 283 | 284 | K 10 | 25078.21399 |
| $\sigma$ 11 | 500 | 503 | K 11 | 54137.67301 |
| $\sigma$ 12 | 390 | 394 | K 12 | −21740.48588 |
| $\sigma$ 13 | 742 | 742 | K 13 | 14944.19251 |
| $\sigma$ 14 | 299 | 300 | K 14 | −41194.49975 |

Discrimination rate = 97.78%
Bo = −830.25865
$\alpha$ = 1
$\beta$ = 0
Number of samples = 89
Concentration varying from 0 to 1000 mg/l
ETC = 38.4492
$R^2$ = 0.9822

The ethanal not originally present in the musts is specifically formed by the yeasts. This permits the presence of yeasts and the start of fermentation to be detected and can be used in the quality index $Q_2$.

ARABITOL

| $\sigma i$ | DE | A | Ki | |
|---|---|---|---|---|
| $\sigma$ 1 | 445 | 446 | K 1 | 34011.16421 |
| $\sigma$ 2 | 374 | 374 | K 2 | −51783.46396 |
| $\sigma$ 3 | 448 | 457 | K 3 | −122987.87178 |
| $\sigma$ 4 | 358 | 358 | K 4 | −93391.60145 |
| $\sigma$ 5 | 353 | 353 | K 5 | 32028.99373 |
| $\sigma$ 6 | 307 | 307 | K 6 | 13702.96397 |
| $\sigma$ 7 | 295 | 295 | K 7 | 53867.88537 |
| $\sigma$ 8 | 562 | 563 | K 8 | 36605.77772 |
| $\sigma$ 9 | 301 | 302 | K 9 | −81872.88535 |
| $\sigma$ 10 | 330 | 332 | K 10 | 105552.06113 |
| $\sigma$ 11 | 400 | 400 | K 11 | 46749.66484 |
| $\sigma$ 12 | 269 | 269 | K 12 | −5973.89318 |
| $\sigma$ 13 | 393 | 393 | K 13 | −39254.22277 |
| $\sigma$ 14 | 382 | 382 | K 14 | 78489.74000 |

ARABITOL -continued

| $\sigma i$ | DE | A | Ki | |
|---|---|---|---|---|
| $\sigma$ 15 | 377 | 378 | K 15 | −53786.09915 |
| $\sigma$ 16 | 768 | 768 | K 16 | 4573.32521 |
| $\sigma$ 17 | 250 | 252 | K 17 | 3159.98168 |
| $\sigma$ 18 | 290 | 290 | K 18 | 13594.96085 |
| $\sigma$ 19 | 384 | 384 | K 19 | −46051.52112 |
| $\sigma$ 20 | 371 | 371 | K 20 | 45257.05498 |

Discrimination rate = 94.21%
Bo = 23.67991
$\alpha$ = 1,0006
$\beta$ = 0,4956
Number of samples = 89
Concentration varying from 0 to 350 mg/l
ETC = 19.7440
$R^2$ = 0.9593

Arbitol has the same properties as ethanal, and can be used in the calculation of the quality index $Q_2$.

METHYL-3-BUTANOL 1

| $\sigma i$ | DE | A | Ki | |
|---|---|---|---|---|
| $\sigma$ 1 | 445 | 445 | K 1 | 37001.13793 |
| $\sigma$ 2 | 451 | 451 | K 2 | −31825.73760 |
| $\sigma$ 3 | 740 | 740 | K 3 | −11537.90703 |
| $\sigma$ 4 | 359 | 360 | K 4 | 2750.26865 |
| $\sigma$ 5 | 294 | 294 | K 5 | 27669.36454 |
| $\sigma$ 6 | 309 | 309 | K 6 | −10792.87694 |
| $\sigma$ 7 | 566 | 568 | K 7 | 12235.25346 |
| $\sigma$ 8 | 379 | 379 | K 8 | −2020.95509 |
| $\sigma$ 9 | 271 | 271 | K 9 | −3134.44842 |
| $\sigma$ 10 | 393 | 393 | K 10 | −8172.41484 |
| $\sigma$ 11 | 399 | 400 | K 11 | −6272.69448 |
| $\sigma$ 12 | 502 | 502 | K 12 | 16729.91741 |
| $\sigma$ 13 | 265 | 266 | K 13 | −1885.60801 |
| $\sigma$ 14 | 283 | 283 | K 14 | 6328.39641 |
| $\sigma$ 15 | 326 | 326 | K 15 | −22107.92011 |

Discrimination rate = 97.28%
Bo = 308.18771
$\alpha$ = 1
$\beta$ = 0
Number of samples = 96
Concentration varying from 0 to 400 mg/l
ETC = 19.4254
$R^2$ = 0.9714

Methyl-3-butanol 1 has substantially the same properties as ethanal, and may be used in the calculation of the quality index $Q_2$.

ISOAMYL ACETATE

| $\sigma i$ | DE | A | Ki | |
|---|---|---|---|---|
| $\sigma$ 1 | 445 | 446 | K 1 | 8869.55722 |
| $\sigma$ 2 | 351 | 351 | K 2 | −4724.52417 |
| $\sigma$ 3 | 331 | 331 | K 3 | 16284.72853 |
| $\sigma$ 4 | 358 | 358 | K 4 | −13187.74050 |
| $\sigma$ 5 | 451 | 451 | K 5 | −18796.27131 |
| $\sigma$ 6 | 378 | 379 | K 6 | −18948.30736 |
| $\sigma$ 7 | 294 | 295 | K 7 | 13557.03424 |
| $\sigma$ 8 | 567 | 567 | K 8 | −8980.89314 |
| $\sigma$ 9 | 301 | 302 | K 9 | −13349.49570 |
| $\sigma$ 10 | 308 | 309 | K 10 | 2551.18673 |
| $\sigma$ 11 | 398 | 398 | K 11 | −7997.38660 |
| $\sigma$ 12 | 683 | 683 | K 12 | −2168.91044 |

-continued

ISOAMYL ACETATE

| σi | DE | A | Ki | |
|---|---|---|---|---|
| σ 13 | 385 | 385 | K 13 | 2529.67798 |
| σ 14 | 393 | 393 | K 14 | −10198.64556 |
| σ 15 | 281 | 281 | K 15 | −1074.13624 |
| σ 16 | 354 | 354 | K 16 | 12906.05284 |
| σ 17 | 270 | 270 | K 17 | −822.14254 |
| σ 18 | 253 | 253 | K 18 | 2550.37446 |
| σ 19 | 256 | 256 | K 19 | −2670.03048 |
| σ 20 | 250 | 250 | K 20 | 1499.44706 |

Discrimination rate = 90.67%
Bo = 93.23514
α = 1
β = 0
Number of samples = 98
Concentration varying from 0 to 100 mg/l
ETC = 8.0368
$R^2$ = 0.9185

Isoamyl acetate has the same properties as ethanal, and may be used in the calculation of the quality index $Q_i$.

GLYCEROL

| σi | DE | A | Ki | |
|---|---|---|---|---|
| σ 1 | 447 | 447 | K 1 | −51.35261 |
| σ 2 | 302 | 302 | K 2 | −50.58692 |
| σ 3 | 366 | 366 | K 3 | 13.52560 |
| σ 4 | 353 | 353 | K 4 | 8.17399 |
| σ 5 | 393 | 396 | K 5 | 30.39023 |
| σ 6 | 741 | 742 | K 6 | 49.85179 |
| σ 7 | 383 | 384 | K 7 | 110.81504 |
| σ 8 | 390 | 390 | K 8 | 254.95298 |
| σ 9 | 334 | 334 | K 9 | 141.55803 |
| σ 10 | 361 | 362 | K 10 | 211.46653 |
| σ 11 | 371 | 371 | K 11 | 219.53447 |
| σ 12 | 274 | 276 | K 12 | −28.56856 |
| σ 13 | 769 | 769 | K 13 | −20.34421 |
| σ 14 | 392 | 392 | K 14 | −89.82594 |
| σ 15 | 450 | 450 | K 15 | 21.01462 |

Discrimination rate = 97.40%
Bo = −2.32923
α = 1
β = 0
Number of samples = 55
Concentration varying from 0 to 25 000 mg/l
ETC = 0.0580
$R^2$ = 0.9728

Glycerol has the same properties as ethanol, and may be used in the calculation of the quality index $Q_2$.

2,3-BUTANEDIOL

| σi | DE | A | Ki | |
|---|---|---|---|---|
| σ 1 | 446 | 446 | K 1 | −61624.13783 |
| σ 2 | 566 | 567 | K 2 | 115022.21030 |
| σ 3 | 358 | 358 | K 3 | 315082.03317 |
| σ 4 | 295 | 295 | K 4 | −25522.71367 |
| σ 5 | 311 | 311 | K 5 | −61376.66922 |
| σ 6 | 352 | 354 | K 6 | −188041.60059 |
| σ 7 | 450 | 452 | K 7 | 108380.73874 |
| σ 8 | 400 | 400 | K 8 | −59989.91275 |
| σ 9 | 738 | 739 | K 9 | −99409.32842 |
| σ 10 | 378 | 379 | K 10 | 256606.18742 |
| σ 11 | 264 | 264 | K 11 | −31295.02573 |
| σ 12 | 258 | 260 | K 12 | 15678.84745 |

2,3-BUTANEDIOL

| σi | DE | A | Ki | |
|---|---|---|---|---|
| σ 13 | 320 | 321 | K 13 | −165106.31604 |
| σ 14 | 331 | 333 | K 14 | 121745.91275 |
| σ 15 | 398 | 398 | K 15 | 11576.64077 |

Discrimination rate = 98.67%
Bo = 354.21365
α = 1
β = 0
Number of samples = 96
Concentration varying from 333 to 1350 mg/l
ETC = 74.6002
$R^2$ = 0.9861

The yeasts and the bacteria produce the 2,3-butanediol. It can be used in the calculation of the quality indices 02, 03 and 04.

ETHYL ACETATE

| σi | DE | A | Ki | |
|---|---|---|---|---|
| σ 1 | 445 | 445 | K 1 | −4022.10920 |
| σ 2 | 450 | 450 | K 2 | −65335.82429 |
| σ 3 | 740 | 740 | K 3 | 29242.22311 |
| σ 4 | 358 | 358 | K 4 | 10502.82006 |
| σ 5 | 301 | 301 | K 5 | −108382.38049 |
| σ 6 | 399 | 399 | K 6 | 19933.58344 |
| σ 7 | 308 | 308 | K 7 | 41565.01236 |
| σ 8 | 329 | 330 | K 8 | 177242.60253 |
| σ 9 | 295 | 295 | K 9 | 33912.39645 |
| σ 10 | 391 | 391 | K 10 | 58902.89916 |
| σ 11 | 260 | 260 | K 11 | 24959.20375 |
| σ 12 | 505 | 505 | K 12 | −100795.64524 |
| σ 13 | 566 | 566 | K 13 | 41291.76755 |
| σ 14 | 269 | 270 | K 14 | −3775.18718 |
| σ 15 | 397 | 397 | K 15 | −55403.16130 |
| σ 16 | 377 | 378 | K 16 | −78470.10709 |
| σ 17 | 382 | 382 | K 17 | 69763.39685 |
| σ 18 | 343 | 345 | K 18 | −102702.52928 |
| σ 19 | 282 | 282 | K 19 | −3911.36127 |
| σ 20 | 770 | 770 | K 20 | −10660.03193 |

Discrimination rate = 96.11%
Bo = 1302.08571
α = 1
β = 0
Number of samples = 98
Concentration varying from 0 to 500 mg/l
ETC = 26.9794
$R^2$ = 0.9608

The ethyl acetate initially not present in the musts is formed specifically by the acid bacteria and certain yeasts. It may be used in the calculation of the quality indices $Q_2$ and $Q_3$.

MANNITOL

| σi | DE | A | Ki | |
|---|---|---|---|---|
| σ 1 | 446 | 446 | K 1 | −3179.89056 |
| σ 2 | 566 | 567 | K 2 | 5001.38528 |
| σ 3 | 358 | 358 | K 3 | 15593.50139 |
| σ 4 | 295 | 295 | K 4 | −1886.50039 |
| σ 5 | 311 | 311 | K 5 | −3637.02250 |
| σ 6 | 352 | 354 | K 6 | −10007.26393 |
| σ 7 | 451 | 451 | K 7 | 5416.46202 |

-continued

MANNITOL

| σi | DE | A | Ki | |
|---|---|---|---|---|
| σ 8 | 400 | 400 | K 8 | −2785.76190 |
| σ 9 | 738 | 739 | K 9 | −6745.93770 |
| σ 10 | 378 | 379 | K 10 | 12399.78063 |
| σ 11 | 264 | 264 | K 11 | −1173.32860 |
| σ 12 | 257 | 260 | K 12 | 919.95926 |
| σ 13 | 321 | 321 | K 13 | −7657.43606 |
| σ 14 | 331 | 332 | K 14 | 6569.68872 |
| σ 15 | 762 | 763 | K 15 | 1477.56746 |

Discrimination rate = 98.70%
Bo = 52.25987
α = 1
β = 0
Number of samples = 98
Concentration varying from 90 to 750 mg/l
ETC = 3.7352
$R^2$ = 0.9859

The mannitol is specifically produced by the lactic acid bacteria and *Botrytis cinerea*. It can be used to calculate Q1 and Q2.

SORBITOL

| σi | DE | A | Ki | |
|---|---|---|---|---|
| σ 1 | 1365 | 1365 | K 1 | −170763.92687 |
| σ 2 | 1724 | 1724 | K 2 | −74236.87161 |
| σ 3 | 1516 | 1520 | K 3 | 17284.26311 |
| σ 4 | 1388 | 1388 | K 4 | 160555.50077 |
| σ 5 | 1165 | 1165 | K 5 | −285759.08492 |
| σ 6 | 1986 | 1986 | K 6 | 25471.99288 |
| σ 7 | 1404 | 1415 | K 7 | 286285.44757 |
| σ 8 | 1057 | 1057 | K 8 | 11876.72404 |
| σ 9 | 2881 | 2881 | K 9 | −505.86779 |
| σ 10 | 1037 | 1037 | K 10 | −10572.17495 |
| σ 11 | 1446 | 1446 | K 11 | −152242.11656 |
| σ 12 | 1222 | 1222 | K 12 | 180946.67117 |
| σ 13 | 1496 | 1496 | K 13 | 134293.16678 |
| σ 14 | 1523 | 1527 | K 14 | −137429.76254 |
| σ 15 | 964 | 964 | K 15 | 6861.61554 |

Discrimination rate = 88.50%
Bo = 2852.12225
α = 0.9993
β = 0.6461
Number of samples = 50
Concentration varying from 30 to 300 mg/l
ETC = 22.3337
$R^2$ = 0.9167

The sorbitol is specifically produced by *Botrytis cinerea*. It can be used to calculate the quality Q2.

GLUCONIC ACID

| σi | DE | A | Ki | |
|---|---|---|---|---|
| σ 1 | 449 | 449 | K 1 | 27.59437 |
| σ 2 | 352 | 352 | K 2 | −494.94507 |
| σ 3 | 333 | 333 | K 3 | 354.10721 |
| σ 4 | 294 | 294 | K 4 | 367.10310 |
| σ 5 | 302 | 302 | K 5 | −157.88863 |
| σ 6 | 396 | 397 | K 6 | −276.03158 |
| σ 7 | 390 | 391 | K 7 | −115.88962 |
| σ 8 | 365 | 370 | K 8 | 2.66976 |
| σ 9 | 377 | 377 | K 9 | 140.25803 |
| σ 10 | 267 | 268 | K 10 | 27.71803 |

-continued

GLUCONIC ACID

| σi | DE | A | Ki | |
|---|---|---|---|---|
| σ 11 | 384 | 384 | K 11 | 51.07514 |
| σ 12 | 741 | 741 | K 12 | −223.32023 |
| σ 13 | 261 | 261 | K 13 | −67.28365 |
| σ 14 | 372 | 372 | K 14 | −29.43258 |
| σ 15 | 364 | 364 | K 15 | −63.25036 |

Discrimination rate = 99.44%
Bo = 3.47339
α = 1
β = 0
Number of samples = 98
Concentration varying from 0 to 8000 mg/l
ETC = 0.1692
$R^2$ = 0.9955

The gluconic acid is specifically produced by *Botrytis cinerea* and can be used in the calculation of the quality index Q1.

MESOINOSITOL

| σi | DE | A | Ki | |
|---|---|---|---|---|
| σ 1 | 445 | 446 | K 1 | −51313.80771 |
| σ 2 | 450 | 450 | K 2 | −42575.49224 |
| σ 3 | 740 | 740 | K 3 | −52662.13173 |
| σ 4 | 358 | 358 | K 4 | −21329.77085 |
| σ 5 | 301 | 301 | K 5 | −175911.52518 |
| σ 6 | 399 | 399 | K 6 | −91799.02350 |
| σ 7 | 308 | 308 | K 7 | 24446.66022 |
| σ 8 | 567 | 567 | K 8 | −3575.37646 |
| σ 9 | 331 | 331 | K 9 | 247459.08477 |
| σ 10 | 295 | 295 | K 10 | 43222.40578 |
| σ 11 | 390 | 390 | K 11 | 51560.39057 |
| σ 12 | 505 | 505 | K 12 | −127663.26606 |
| σ 13 | 260 | 260 | K 13 | 49854.22008 |
| σ 14 | 269 | 269 | K 14 | −11978.62572 |
| σ 15 | 377 | 378 | K 15 | −59824.90209 |

Discrimination rate = 94.25%
Bo = 3246.66966
α = 1
β = 0
Number of samples = 96
Concentration varying from 220 to 730 mg/l
ETC = 69.1944
$R^2$ = 0.9380

Mesoinositol is naturally present in the musts and is produced by the fermentive growth. It may be used in the calculation of the fermentability quality index $Q_5$.

This example indicates that the various parameters can be used with an excellent reliability to calculate the objective quality indices of the vinification compositions. The correlation coefficients are in all cases greater than 0.90; and even in most of the cases greater than 0.95, and from a relatively low number of calibration samples. The concentration values are obtained according to the invention (from the spectrum) in less the one minute for each sample; each quality index can, for example, be calculated from the simple sum of values obtained for each characteristic parameter that makes it up, and compared to a reference value of a vinification composition considered to be of good quality according to oenological theory or practice.

The invention can be the object of numerous variants in relation to the above description, which is given only by way of non-limiting example.

What is claimed is:

1. A method for the objective qualitative analysis of liquid vinification compositions, characterised in that:
   an initial configuration and calibration step (13) is carried out during which:
      a group of characteristic parameters are selected, the characteristic parameters being capable of characterising the quality of a vinification composition to be analysed, and comprising the concentration levels in the vinification composition of characteristic compounds, chosen among at least a compound produced by *Botrytis cinerea*, at least a compound produced by yeasts, and at least a compound produced by acetic bacteria, and at least a compound produced by lactic acid bacteria,
      calibration values ($\sigma_1$, $K_2$, $B_0$) of spectroscopic criteria are determined and recorded for each characteristic parameter, the spectroscopic criteria being chosen to enable evaluation of the characteristic parameter in a vinification composition from an infrared absorption spectrum, which can be generated from a sample of this vinification composition,
   for each vinification composition to be analysed:
      a spectroscopic analysis (17, 18) is carried out during which a continuous infrared absorption spectrum of a sample of this vinification composition is generated,
      the spectroscopic criteria of each characteristic parameter are applied to the said continuous spectrum in such a way that the value ($V_p$) of this characteristic parameter in the vinification composition is evaluated by automatic calculation (19).

2. A method according to claim 1, characterised in that the group of characteristic parameters comprises the concentration of each of the characteristic compounds, belonging to the group consisting of gluconic acid, ethanal, ethyl acetate, arabitol, mannitol, sorbitol, 2,3-butanediol, methyl-3 butanol-1, glycerol, mesioniotol and isoamyl acetate.

3. A method according to claim 1, characterised in that the continuous spectrum is generated by Fourier transform interferometric spectroscopy.

4. A method according to claim 1, characterised in that the spectroscopic criteria are chosen to enable evaluation of each characteristic parameter in a vinification composition from a near and mid infrared absorption spectrum, and in that the near and mid infrared continuous spectrum of each vinification composition to be analysed is generated.

5. A method according to claim 1, characterised in that at least an objective quality index ($Q_j$) of the vinification composition is calculated as a function of the said value ($V_p$) evaluated from at least a characteristic parameter of the vinification composition to be analysed.

6. A method according to claim 5, characterised in that the function is a polynomial function.

7. A method according to claim 5, characterised in that there are calculated:
   a first quality index, representing the attack on the harvest by *Botrytis cinerea*, at least as a function of the value of concentration levels of gluconic acid, mannitol and sorbitol evaluated from the continuous spectrum by application of spectroscopic criteria,
   a second quality index, representing the attack by yeasts, at least as a function of the value of the concentration levels of ethanal, ethyl acetate, arabitol, of 2,3-butanediol, of methyl-3 butanol-1, of glycerol, of mesoinositol and of isoamyl acetate evaluated from the continuous spectrum by application of spectroscopic criteria,
   a third quality index representing the attack by acetic bacteria, at least as a function of values of the concentration levels of acetic acid, ethyl acetate and of 2,3-butanediol evaluated from the continuous spectrum obtained by application of spectroscopic criteria,
   a fourth quality index representing the attack by lactic acid bacteria, at least as function of the value of concentration levels of lactic acid, mannitol and of 2,3-butanediol, evaluated from the continuous spectrum obtained by application of spectroscopic criteria,
   and a fifth quality index representing the fermentation ability, at least as a function of the value of the concentration of mesoinositol.

8. A method according to claim 5, characterised in that each characteristic parameter is evaluated and each quality index ($Q_j$) is calculated by data processing immediately after the spectroscopic analysis step has been carried out.

9. A method according to claim 1, characterised in that the spectroscopic criteria comprise for each characteristic parameter, for a selection of an integral number N of sectral bands σi of predetermined wavelengths, the value of the luminescence spectral density Li of the said continuous spectrum, and in that a value $V_p$ of the characteristic parameter is calculated according to the formula:

$$V_p = Bo + \sum_{i=1}^{N} Ki \; Li$$

where Bo and Ki are predetermined coefficients.

10. A method according to claim 9, characterised in that each N lies between 5 and 30.

11. A method according to claim, characterised in that the group of characteristic parameters further comprises alcoholic volumetric strength; total sugar content; total acidity; pH; concentration of acetic acid; concentration of malic acid; concentration of tartaric acid; concentration of lactic acid; and content of phenolic compounds.

12. A device for objective qualitative analysis of liquid vinification compositions, characterised in that it comprises:
   memory means (8) in which the calibration values (($\sigma_1$, $K_1$, $B_0$)) of spectroscopic criteria are recorded for a group of characteristic parameters capable of characterising the quality of a vinification composition to be analysed, this group comprising the concentration levels in the vinification composition of characteristic compounds selected from at least a compound produced by *Botrytis cinerea*, at least a compound produced by yeasts, and at least a compound produced by acetic bacteria, at least a compound produced by lactic acid bacteria, the said spectroscopic criteria being selected for each characteristic parameter to enable evaluation of the characteristic parameter in a vinification composition from an infrared absorption spectrum that can be generated from a sample of this vinification composition,
   spectroscopic analysis means (1, 2, 3, 4, 6) for collecting a sample of vinification composition and generating an infrared continuous spectrum of this sample,
   calculation means (7) arranged to apply the spectroscopic criteria of each characteristic parameter to the sad continuous spectrum and to evaluate by automatic calculation the value ($V_P$) of this characteristic parameter in the vinification composition.

13. A device according to claim 12, characterised in that the group of characteristic parameters comprises the concentration of each of the characteristic compounds belonging to the group consisting of gluconic acid, ethanol, ethyl acetate, arabitol, mannitol, sorbitol, 2,3-butanediol, methyl-3 butanol-1, glycerol, mesoinositol and isoamyl acetate.

14. A device according to claim 12, characterised in that the spectroscopic analysis means (1, 2, 3, 4, 6) comprise a Fourier transform interferometric spectrometer.

15. A device according to claim 12, characterised in that the selection criteria are chosen for each characteristic parameter to enable evaluation of the characteristic parameter in a vinification composition from a near and mid infrared spectrum, and in that the spectroscopic analysis means (1, 2, 3, 4, 6) are arranged to generate near and mid infrared continuous absorption spectra.

16. A device according to claim 12, characterised in that the calculation means (7) are arranged to calculate automatically at least an objective quality index ($Q_j$) of the vinification composition as a function of this value ($V_P$) evaluated from at least a characteristic parameter for the vinification composition to be analysed.

17. A device according to claim 16, characterised in that the function is a polynomial function.

18. A device according to claim 16, characterised in that the calculation means (7) are arranged to calculate:

- a first quality index, representing the attack on the harvest by *Botrytis cinerea*, at least as a function of the value of concentration levels of gluconic acid, mannitol and sorbitol evaluated from the continuous spectrum by application of spectroscopic criteria,
- a second quality index, representing the attack by yeasts, at least as a function of the value of the concentration levels of ethanol, ethyl acetate, arabitol, of 2,3-butanediol, of methyl-3 butanol-1, of glycerol, of mesoinositol and of isoamyl acetate evaluated from the continuous spectrum by application of spectroscopic criteria,
- a third quality index representing the attack by acetic bacteria, at least as a function of values of the concentration levels of acetic acid, ethyl acetate and of 2,3-butanediol evaluated from the continuous spectrum obtained by application of spectroscopic criteria,
- a fourth quality index representing the attack by lactic acid bacteria, at least as function of the value of concentration levels of lactic acid, mannitol and of 2,3-butanediol, evaluated from the continuous spectrum obtained by application of spectroscopic criteria,
- and a fifth quality index representing the fermentation ability, is calculated at least as a function of the value of the concentration of mesoinositol.

19. A device according to claim 16, characterised in that the calculation means (7) are arranged to evaluate each characteristic parameter and to calculate each quality index $Q_j$ by data processing immediately after the generation of the continuous spectrum by the spectroscopic analysis means (1, 2, 3, 4, 6), and to provide the results of these calculations to means (10) that are read by a user.

20. A device according to claim 18 characterised in that the means (10) that are read comprise means for printing a report of results.

21. A device according to claim 12, characterised in that for each characteristic parameter, the calibration values comprise an integral number N of spectral bands σi of predetermined wavelengths and coefficients Ki and Bo, and in that the calculation means (7) are arranged to calculate a value $V_P$ of the characteristic parameter from values of the luminescence spectral density Li of the said continuous spectrum obtained for the N spectral bands σi, according to the formula:

$$Vp = Bo + \sum_{i=1}^{N} Ki \; Li.$$

22. A device according to claim 21, characterised in that N is a number between 5 and 30.

23. A device according to claim 12, characterised in that the group of characteristic parameters further comprises alcoholic strength; total sugar content; total acidity; pH; concentration of acetic acid;

concentration of malic acid; concentration of tartaric acid; concentration of lactic acid; and content of phenolic compounds.

* * * * *